United States Patent [19]
Matz

[11] 4,144,165
[45] Mar. 13, 1979

[54] DIALYZER, SYSTEM AND DIALYSIS METHOD

[76] Inventor: Andrew R. Matz, Hare's Hill Rd., P.O. Box 445, Kimberton, Pa. 19442

[21] Appl. No.: 858,414

[22] Filed: Dec. 7, 1977

[51] Int. Cl.² .................... B01D 31/00; B01D 13/00
[52] U.S. Cl. ........................... 210/22 C; 210/321 A; 210/416 M
[58] Field of Search ................ 210/22, 321 R, 321 A, 210/321 B, 416 M; 23/230 B, 274

[56] References Cited
U.S. PATENT DOCUMENTS

| | | | |
|---|---|---|---|
| 2,985,587 | 5/1961 | Hoch et al. | 210/22 |
| 3,199,680 | 8/1965 | Schiff | 210/321 R |

Primary Examiner—Frank A. Spear, Jr.
Attorney, Agent, or Firm—Maleson, Rosenberg & Bilker

[57] ABSTRACT

A dialyzer and a dialysis system particularly adapted to fast dialysis and avoidance of contamination or spillage. Adjustable upper and lower clamp units are provided on a central shaft. Means are provided to securely mount a plurality of dialysis bags around the entire periphery of the clamping units and to provide adequate bath circulation through the relatively confined core volume. The individual dialysis bag may be accurately filled or emptied while in a fully installed position on the dialyzer. The circulating pump is a pair of openings in the bottom clamp unit. The top of each bag is always open to receive a syringe needle. The rotating motor is isolated from the bath.

16 Claims, 5 Drawing Figures

DIALYZER, SYSTEM AND DIALYSIS METHOD

BACKGROUND OF THE INVENTION

1. Field of the Invention

This invention relates to dialysis and dialyzer apparatus. It relates to a dialysis system including a dialyzer. This invention is particularly directed toward the use of dialysis in medical diagnostic activity, in which it is desired to separate from a sample molecules of less than a given predetermined size by having them dialyze through a membrane into a surrounding bath. The invention is particularly adapted to use in clinical medical laboratories in which factors of speed, accuracy, and costs are important.

2. Prior Art

Dialysis is a known technique, including its use in the field of medical diagnostics. Prior art apparatus is known. Some of this prior art apparatus is relatively expensive and large automatic machinery. Some of the prior expedients include the suspension of relatively large elongated tubes of membrane from one end in an agitated bath with the tubes free to move relatively to each other.

Another prior art expedient is a dialysis bag clamping system utilizing a magnetic stirrer and having the capability of providing only for a limited number of dialysis bags. Such a device is known as the Crowe-Englander dialyzer available from Hoefer Scientific Instruments, Inc.

Other prior art is exemplified in such U.S. Pat. Nos. as 3,672,509; 2,985,587; 3,788,471; 3,503,877; 3,783,127; 3,811,573; and 3,596,882.

The present invention has many advantages over what can be found in any example of the prior art. These advantages include lower costs and higher speed in its class of equipment. An advantage is easy adjustability to accommodate different quantities of samples to be analyzed. An advantage is that wetted bags can be mounted in the operative position before loading. This permits accurate loading and unloading without handling of the bags and possible contamination or loss of sample. Other advantages include prevention of distortion of results by inadvertent contacting of bags during the dialysis process, the ability to make interim checks on the process, and the ability to determine whether there has been any inadvertent loss by leakage during the process.

Another advantage is the increased temperature stability due to the organization of the present dialysis system. Another advantage is a much greater speed of the dialysis process due to the greater efficiency of membrane surface circulation and a higher ratio of membrane surface to specimen volume than was heretofore available. An advantage lies in the provision of the circulating function through extremely simple, reliable, and inexpensive means. Other advantages are discussed in the following specification and will be apparent to those skilled in the art.

SUMMARY OF THE INVENTION

This invention is a small, fast, reliable, accurate dialyzer particularly suitable for non-automated, relatively small scale diagnostic analysis. The dialyzer system includes a container for a bath, generally distilled water, the dialyzer itself, and a motor and connecting means from the motor to the dialyzer, with the motor mounted above and isolated from the bath so as to avoid affecting the temperature stability of the bath.

The dialyzer itself generally comprises a central shaft on which are mounted an upper clamp unit and a lower clamp unit. The distance between the clamp units is adjustable to accommodate dialysis bags of different lengths. The entire periphery of the clamp units may be surrounded with an array of vertically oriented dialysis bags. In the preferred embodiment, there are twelve such bags, three on each side of the square clamp units.

The lower clamp unit has clamping bars to secure the bottoms of the dialysis bags and seal them. The lower clamp unit also is provided with a pair of oppositely slanted holes which together form a simple, elegant circulating pumping means to provide forced circulation of the bath into the central core of the dialyzer, that is, into that volume of the bath bounded by the vertical curtain of dialyzer bags.

The upper clamp unit is provided with a plurality of vertically aligned grooves or channels, with one channel corresponding to each bag. The upper portion of each bag is passed through its channel. A rigid filling tube is inserted in the upper portion of each bag, positioned within the channel. The filling tube extends above the end of the bag and the upper clamp unit.

DESCRIPTION OF THE PREFERRED EMBODIMENTS

Figures 1, 2:
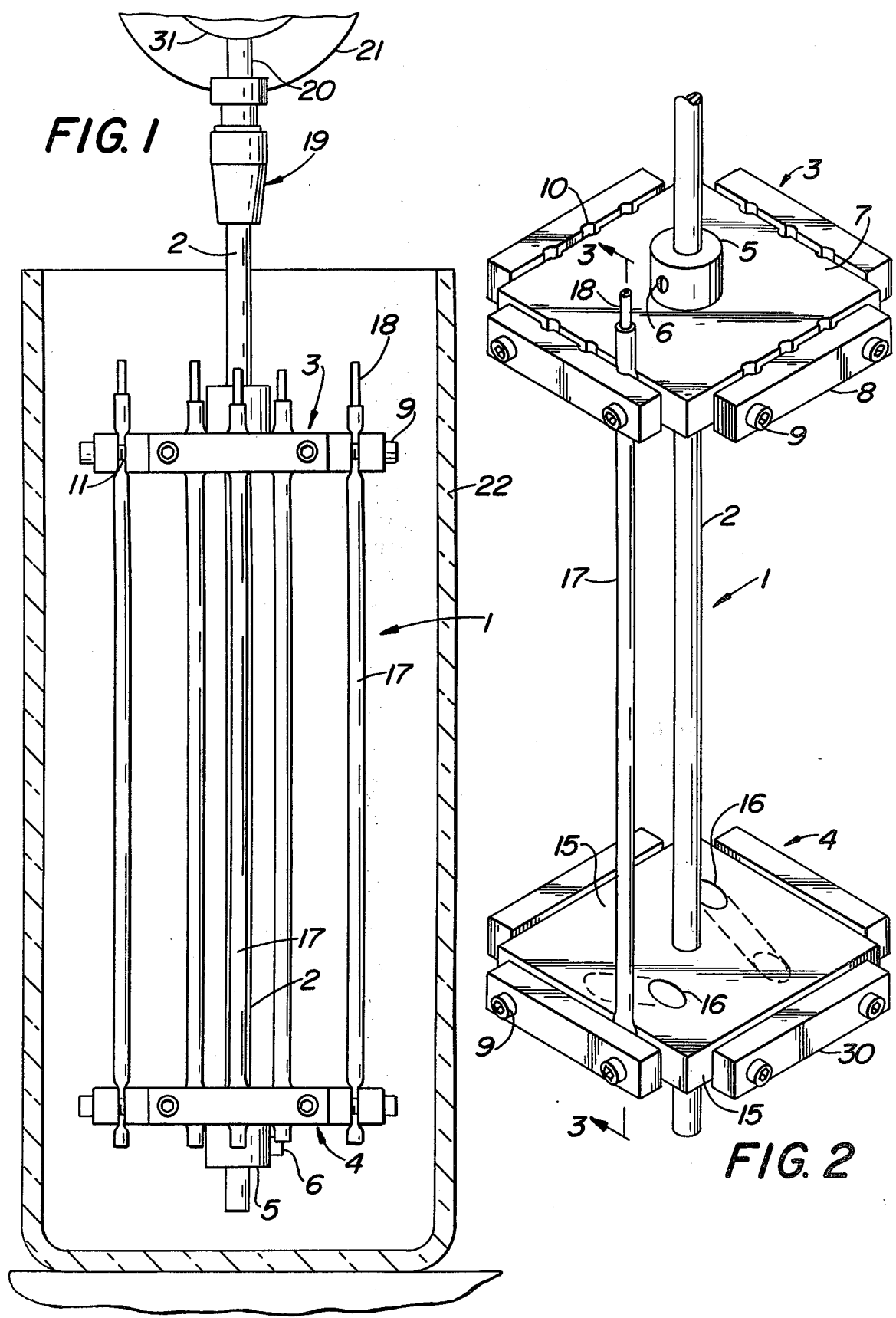
FIG. 1 is a front elevation view, partly in cross-section of the dialyzer.
FIG. 2 is a perspective view of the dialyzer, showing one dialysis membrane bag in place.

The dialyzer can best be initially described in connection with FIG. 2. The dialyzer, generally designated 1, comprises means for supporting a plurality of membraneous dialysis bags for movement relative to an external bath. In comprises a central shaft 2. An upper clamp unit, generally designated 3, and a lower clamp unit generally designated 4, are provided. The upper clamp unit comprises an upper clamp central block 7. This central block is provided with a hole through the center thereof, and has a collar 5 surrounding the hole. A set screw 6 is provided through an appropriately threaded hole in the collar 5. The central block 7 may thus be selectively firmly positioned at any point along central shaft 2 by tightening the set screw 6. The central block 7 is square in its horizontal shape. Along each of the four sides of the square there is provided an upper clamp bar 8. Each of the upper clamp bars 8 is retained on the central block 7 by a pair of clamp bolts 9.

Each of the bars 8 has an inner face which opposes an outer face of the control block 7. The inner face of each bar 8 is provided with three vertically aligned substantially semi-circular grooves or channels 10. The opposing outer face of the control block 7 is provided with opposing, matching and aligned vertically aligned substantially semi-circular channels or grooves. The preferable number of such grooves on each clamping bar 8 and hence on each of the four sides of the central block 7 is three. It is apparent that each channel 10 and its opposing channel, together form an approximately circular vertical channel.

The lower clamp unit 4 comprises a lower clamp central block 15. The central block 15 is square in its horizontal configuration and its outer dimensions and configuration are the same as that of upper central block 7. As is better shown in FIG. 1, the lower clamp central block 15 is provided with a hole through the center thereof. The hole is surrounded by a collar 5. In the same manner as has been described in connection with the collar 5 on central block 7, the lower clamp central block 15's collar 5 is provided with a set screw so that the lower clamp unit 4 may be selectively moved along shaft 2 when the set screw is loosened, and firmly fastened in place when the set screw is tightened.

The lower clamp unit 4 is provided with four lower clamp bars 30. Each of these lower clamp bars 30 is opposed to one of the four sides or outer faces of the lower clamp block 15. Each of the bars 30 is retained against its opposing outer face or edge of the central block 15 by a pair of clamp bolts 9. The organization of the lower clamp bars and lower clamp block is the same as the organization of the upper clamp bars and the upper clamp block. The differences in structure between the upper clamp unit and the lower clamp unit 4 are as follows. The lower clamp unit 4 does not have the plurality of vertically aligned grooves or channels. Instead, the inner faces of the lower clamp bars 30 and the corresponding and opposing outer faces of the lower clamp central block 15 are flat. The lower clamp central block does however have structure that is not found in the upper clamp block. This structure is a pair of inclined openings 16, each running from the upper face to the lower face of the lower clamp central block 15. As best shown in FIG. 2, these two inclined openings are mounted on diametrically opposed sides of the central shaft 2, and their slants or inclination from the vertical, are in opposite directions from each other. Together, these inclined openings, organized as shown and described, comprise a pump. The two sections of inclined openings 16 amount to the equivalent of a section of a screw pump, that is, a pump utilizing the Archimedes Principle.

The upper clamp unit 3 and the lower clamp unit 4 are affixed on the shaft 2, spaced apart from each other with their sides aligned with each other. For better illustration, only a single dialysis bag 17 is shown retained in the dialyzer 1 by being clamped between the upper clamp central block 7 and the lower clamp central block 15. The bag 17 is vertically aligned, and at the upper clamp, it passes through the groove or channel 10. It is apparent that the dialyzer can accommodate twelve such bags 17, each positioned in one of the illustrated grooves 10. A more detailed description of certain aspects of the upper clamp unit, the lower clamp unit and the dialysis bag is better made below in connection with FIGS. 3, 4, and 5.

The complete structure making up an operating dialysis apparatus is best described in connection with FIG. 1. The dialyzer 10 is shown suspended in a container 22. This container is deeper than the distance between the upper and lower clamp units. Some of the bags 17 are shown installed. The central shaft 2 is extended upwards to a chuck 19. This connects the dialyzer 1 with a drive shaft 20. In the preferred embodiment, the drive shaft 20 runs to a right angle drive 31, which in turn is driven by a motor 21. The motor 21 is held in position by being clamped to a stand (not shown), or by being positioned as shown in any conventional manner. The motor is operated so that the dialyzer 1 is rotated in a clockwise direction, in the particular embodiment shown. In this mode of rotation, the inclined openings 16 pump liquid from the lower portion of liquid contained in the container 22 into the volume generally defined as between the plane of the dialysis bag 17 and the central shaft 2, and between the upper and lower central blocks. It is apparent that this pumped liquid may flow out again into the general volume of container 22 between the bags 17, and this is desired, since the purpose of the pump means 16 is to provide circulation.

In FIG. 1, the dialyzer is shown in its operating condition. For better illustration, the presence of the water in container 22 has not been shown. The water level is at least as high as the upper clamped portion of the dialysis bags 17. The water level is lower than the upper edge of filling tubes 18. All twelve dialysis bags 17 are in place in the showing of FIG. 1. As is more fully described below, the dialyzer 1 is rotated by means of motor 21, the pumping action circulates the surrounding water and the dialysis takes place.

Figure 3:
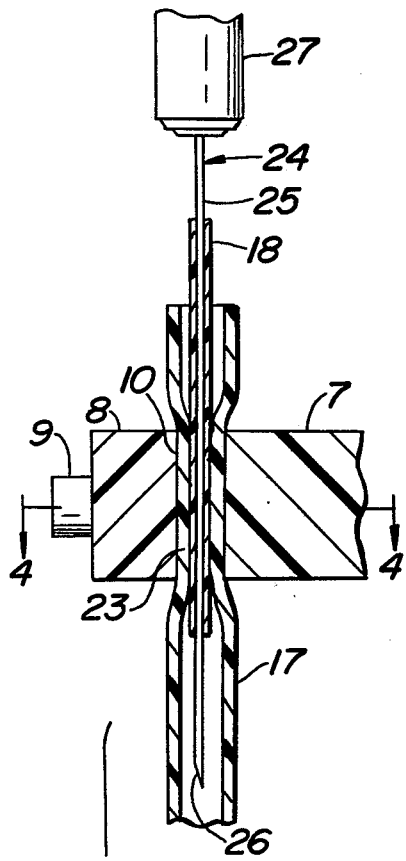
FIG. 3 is a cross-sectional view taken along line 3—3 of FIG. 2, partly fragmented and broken away in the middle section to show the top and bottom portions.
Figure 4:
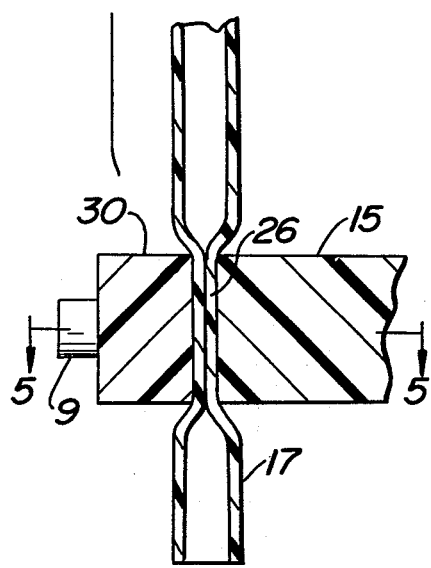
FIG. 4 is a cross-sectional view taken along line 4—4 of FIG. 3.
Figure 4:
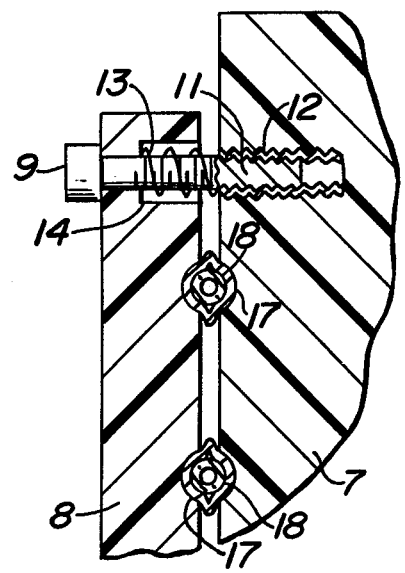

FIG. 3 shows in more detail the upper and lower clamping elements in cooperation with the bag and other elements. Each clamp bolt 9 is provided with a threaded portion 11, as well as a conventional head. The head may be knurled and also may be provided with an internal socket to receive a hex wrench. Each upper clamp bar 8 and each lower clamp bar 30 is provided with a pair of holes, each to receive a clamp bolt 9. Corresponding openings are provided in the outer edges or faces of both the upper and lower clamp blocks. As best shown in FIG. 4, these bolt-receiving holes in the clamp blocks are each provided with a threaded metal insert 12. The threaded portion 11 of bolt 9 coacts with the threaded metal insert 12.

Figure 5:
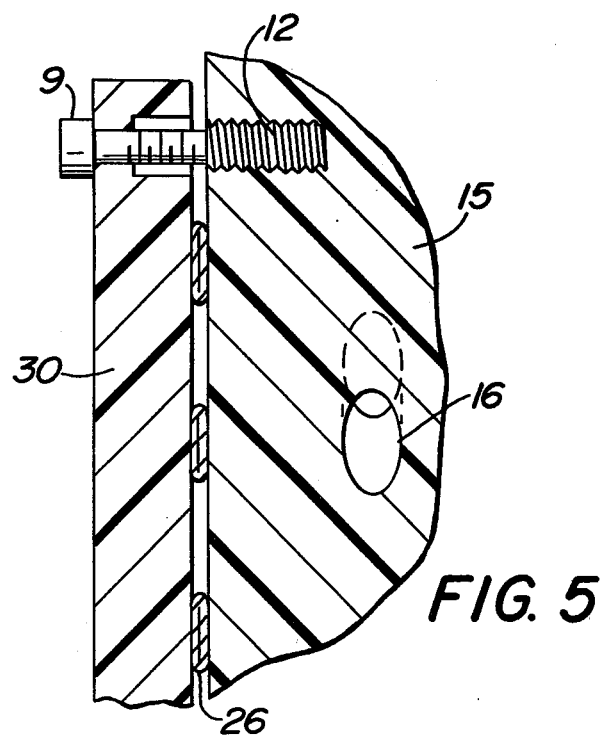
FIG. 5 is a cross-sectional view taken along line 5—5 of FIG. 3.

Each bolt is provided with a helical spring 13, as best shown in FIG. 4. One end of this bears against the outer face or edge of the appropriate clamp block 7 or 30. The other end of the spring 13 bears against the appropriate upper or lower bar 8 or 30. As shown in FIGS. 4 and 5, a recess is provided in the bar to accommodate the spring 13.

As best shown in the bottom portion of FIG. 3, the dialysis bag 17, which is an elongated tube open at both ends, extends between the lower clamp block 15 and the lower clamp bar 30. When the bolts 9 are tightened, the bottom of the dialysis bag 17 is closed and sealed by the clamping action.

The detailed structure of the interaction of the tube 17 and the upper clamp unit 3 is shown in the top portion of FIG. 3. As has been described, the bag 17 is vertically aligned with a channel 10. A small rigid tube 18 is provided, partly inside and partly outside dialysis bag 17, extending above the upper end of the dialysis bag. This rigid filling tube 18 extends through the extent of channel 10. It is apparent that when the upper clamp bar 8 is tightened against the upper clamp central block 7, the filling tube 18 is clamped tightly in the channel 10, inside the walls of the dialysis bag 17, and an opening into the bag 17 is maintained thereby. FIG. 3, in the top portion, additionally shows a filling, inflating, and exhausting means generally designated 24. It comprises a syringe 27 with a hypodermic needle 25. The size of the hypodermic needle is such that it may pass through the opening in filling tube 18. The hypodermic needle 25 is conventionally provided with a beveled tip 26.

Appropriate and preferred dimensions and materials are described. The tank 22 may be six inches in diameter with a height of 18 or 20 inches. Its capacity, full, is 6.5 liters. In practice it is filled with water to about 5 liters.

One satisfactory motor 21 is a Fisher Full Torque Motor obtainable from Fisher Scientific Company. This is a small fraction of a horsepower motor. The motor comes equipped with the right angle drive 31. It is provided with a variostat, that is, a potentiometer, to adjust the speed. The speed range of the driven central shaft 2 is on the order of 100 rpm. The motor is mounted on any type of conventional mount, for example, a laboratory clamp mount. The motor, the right angle drive, the speed varying means, and the coupling means, generally comprising an adjustable chuck 19, are all standard obtainable conventional items well known in the art.

In the dialyzer 1 itself, the central shaft 2, the springs 13 and the clamp bolts 9 are stainless steel. The other parts are transparent plastic, preferably methyl methacrylate. The edges of the clamping members are provided with small bevels or chamfers, not shown, to avoid damage to the delicate bags 17. As has been described, the bolt receiving holes in the central blocks are provided with threaded metal inserts. This is because it has been found preferable to have all moveable or adjustable parts be metal to metal to avoid undue wear. For the same reason, it has been found preferable to provide the spring-containing recesses in the bars, as have been described, with metal liners or sockets, to avoid wear on the plastic.

The rigid filling tube 18 is transparent plastic. It has an ID equivalent to a 28 gage needle. Such tubing is conventionally available and is known as micromedic tubing. The syringe 27 may be a standard syringe of 5cc capacity and the needle 25 attached thereto is an 18 gage needle.

The dialysis bags 17 are semi-permeable membranes, made of cellulose. The thickness of the bag membrane is generally less than 1/1000ths of an inch. The diameter of the bags is on the order of ¼ of an inch. The membranes have fixed pore characteristics which act as a molecular sieve. They are commercially available from a number of suppliers and are well known in the art. They normally come commercially in the form of rolls of tubing, supplied dry, to be cut to length by the user.

The container 22 is preferably of transparent glass.

The shaft 2 may be 18 inches long and ¼ inch in diameter. Each central block may have a horizontal side dimension of three inches, and a thickness of ½ inch. Each clamping bar may have a length of 2⅜ inches and a horizontal thickness of ¼ inch, with the height being the same as the width of the central block. Each channel 10 may have a diameter on the order of 1/16 of an inch.

The preferred rotational speed of the dialyzer is 90–100 rpm. Below this speed range, there is an increasing length of time required for satisfactory dialysis to take place. It has been found that 60 rpm should be considered the practical lower limit of rotational speed to avoid excessively long processing times. It has been found that above about 100 rpm, there is a relatively small gain in dialysis speed, with a continually greater risk of damage to the bags because of the increased stress on them. Therefore, 100 rpm is the preferred upper limit of rotational speed. The preferred operation has been described. The distance between the upper and lower clamp units is set to the desired length, depending on the volume of liquid to be dialyzed. The set screws 6 are then tightened to hold the clamp units at that length. Up to twelve pieces of dialysis bag 17 are cut from the roll, each to the desired length. They are then wet and the bottom of each bag is clamped in the lower clamp unit 4 as has been described. Then, a filling tube 18 is inserted into the top of each bag, which is aligned in its appropriate channel 10. As has been described, three bags are provided on each side of the blocks. The upper clamp bolts 9 are then tightened as has been described.

It is customary procedure to test the integrity of the bags and seals by partly inflating each bag. This is done either by mouth blowing into each tube 18, or the syringe and hypodermic needle means as illustrated in FIG. 3 may be used. A 5cc syringe and an 18 gage needle is provided, with the syringe being filled with air. The syringe is depressed to force air into the bag and inflate it, thus carrying out the test.

The dialyzer 1 is now mounted in the chuck 19. The liquid samples to be analyzed are then individually "injected" through the ends of the tubes 18 into the interior of the respective bags 16, using a filling means 24, comprising a syringe and needle. No further sealing is necessary. The appropriate level of water to cover the operating surface of the bag 17 is provided in container 22, and maintained at the appropriate temperature. The time and temperature characteristics of the dialysis process itself are well known in the dialysis art, and are not per se the subject of the present invention.

Depending on the type of analysis being performed, within the known art, the temperature conditions may be very important and the run may be conducted in a refrigerated environment.

A typical program would be four runs of thirty minutes each, with a change of water after each run, followed a three hour run. During the three hour run, instead of water, specific ions are placed in the liquid in container 22 and a reverse dialysis is accomplished, for the purpose of obtaining ionic equilibrium inside and outside of the bag. This technique in the art of dialysis, considered theoretically, is well known in the art, and has been accomplished by other known apparatus, and is not in itself the subject of this invention.

When the entire dialysis process is complete, a exhausting means 24 is utilized. This is exactly as illustrated in FIG. 3, except that the needle 25 is longer, on the order of 15 inches long, so that it can reach down to the bottom of the bag. The contents of the bag can then be withdrawn by raising the plunger of the syringe.

An alternate way to empty the bag 17 after the dialysis is completed, is to open the bottom clamp and permit the contents of the bags to drain.

If the syringe method of removal is used, it is possible then to flush the interior of the bag and reuse it for another specimen. It is also possible to remove all or a portion of the specimen from the bag, using the syringe method, for an interim test and then to replace it for further processing if desired.

It is understood that the use of stainless steel, glass, and methyl methacrylate are preferable, as described, because they do not leach any contaminants into the bath. It is also apparent that other materials having the necessary chemical and physical properties, as known, may be utilized.

No contribution to the theory of dialysis itself is intended as part of this present invention, and it is apparent that the method and apparatus of this present invention are applicable to all appropriate operations utilizing the known theories and techniques of dialysis. Some observations are made however, to more particularly indicate the uses of the present invention. The liquid inserted in the bag to be analyzed is a mixture of different size molecules. The membrane has given pore sizes. Generally and normally distilled water is used outside of the bags, within the container, as a bath. Molecules having a diameter smaller than the pore diameter of the membrane migrate through to the bath until there is an equality of concentration of molecules of this size on both sides of the membrane, at which time the system comes to equilibrium. Then, when the outside bath water is changed, there is a further migration as aforesaid. The process can be repeated until the amount of moelcules under a given diameter in the sample can be reduced to almost any desired amount, approaching zero.

Then, the contents of the dialysis bag, which are known to contain only molecules of a certain size or larger, are subjected to further and other analytical procedures which are not part of this invention. For example, they may be subjected to electrofluorisis.

One example of the use of this invention arises when amonium sulphate is used to precipitate long chain protein molecules from macerated tissue specimens. It is necessary to get the amonium sulphate out of the specimen, because otherwise the later analytical procedures would be misled by the amonium sulphate. The dialysis process, carried out in accord with this invention, removes the amonium sulphate ions from the specimen.

Another example of the use of this invention is in blood analysis. Blood specimen cells are ruptured sonicly. Then, by dialysis, salts, fibrinogen, and in general all the smaller size molecules (which generally means lower molecular weight molecules) are removed from the specimen, leaving only the macro-molecules. For some purposes this is a very valuable analytical step. On important analytical end purpose in blood analysis is to detect the presence of C.E.A. (Carcinoembryonic Antigen). It has been found that the presence of C.E.A. can be diagnostic of cancer in a patient. Another purpose is for isolating materials useful for preparation of immunological materials.

There are a number of advantages in the present invention. These are discussed below, perhaps not exhaustively. This invention contemplates and permits the simultaneous processing of up to twelve separate dialysis bags. Perhaps more than the actual number, the advantage lies in the use of the entire periphery of the central blocks to support dialysis bags. The productive capacity of a unit of this physical size is thus greatly increased.

It has been found previously not practical to simply add on bags around the periphery as is done in this invention, because the addition of bags simultaneously serves to cut down free circulation of the bath, usually distilled water, and thus, the apparent increase in productive capacity is offset by less efficient dialysis and therefore longer processing times. The elegant and simple expedient of providing the slanted openings 16 in the bottom central block 15, as has been described, overcomes the circulation problem. As has been explained, the pair of openings serve as a circulating pump and force the bath liquid into that sector which would otherwise tend to be relatively stagnant. It has been found that this moves the central core volume of water sufficiently to permit the closed "curtain wall" of bags to be provided around the periphery.

The use of set screw mountings on the collars of the upper and lower blocks 7 and 15 permit the use of different lengths of bags. Thus, it is apparent that the availability of different bag lengths and different numbers of bags in a given run provide a great deal of flexibility in application.

Another important advantage is that the wetted bags can be mounted on the dialyzer before they are loaded with the material to be analyzed. In previously known devices, it was necessary to load the bags before they were fully secured to the dialyzer. Such prior art procedures had a potential for spillage of the sample. The present invention removes this potential. In the present invention, all the bags to be used are firmly clamped at both top and bottom before it becomes necessary to load them with sample to be analyzed.

The use of the spring loaded clamps, as described, permits insertion and removal of bags in a dialyzer without complete physical removal of the clamp from the unit as a whole. That is, when the bolts 9 are loosened, the springs force the bars away from the central blocks to permit easy insertion or removal of the portions of the bag to be clamped.

Another advantage of the present invention over certain other prior art is that the present structure permits the motor to be mounted above the tank and isolated from it. This removes the possibility of heat transfer from the motor to the tank. In some prior art devices, the motor is mounted below the tank and drives the dialyzer support through a magnetic coupling. For long runs, particularly where temperature stability is important or where there is a refrigerated enviornment necessary, this unwanted heat is detrimental. This problem is obviated by the present invention.

Another important advantage lies in the fact that the time for each run and the total running time for a full processing are very substantially less in this invention's use than with some prior art expedients. For example, a more common dialysis method and apparatus involves tubing of perhaps an inch in diameter and quite long, tied at each end manually and hung from a string in a tank with agitated water. From time to time the water is flushed. This type of dialysis may take perhaps forty-eight hours to produce results. On the other hand, with the present invention, overall equivalent processing times, including multiple runs, may be on the order of five hours. Some of the reasons for this improvement are the ability of the present invention to use smaller diameter dialysis bags, thus bringing more of the sample in contact with the membrane. The use of the multiple bags and the ease of loading them makes up for the loss of volume introduced by decreasing the bag diameter. Another reason is the efficient circulation enviornment provided by the present invention. Thus, the present invention is very fast, efficient and reliable. Another advantage is that this entire apparatus is very much cheaper than many of the prior art machines commercially available.

Another advantage is that there is much less potential for contaminating the specimens with the present invention than with some of the prior art devices. It is apparent that being able to handle the specimen entirely with syringes, both to load and unload, and the ease of handling the bags after they are firmly fixed in place, al contribute to this advantage. Furthermore, in many o: the prior art devices, where the bags are suspended only at one end, they inadvertently touch each other at times through the cycle and thus inhibit the dialysis process and tend to produce false results. This type of problem is actually a common one in presently available prior art.

The use of the syringe loading and unloading in the present invention produces another advantage. This arises because such syringes are commonly calibrated, and it is thus possible, without introducing any significant extra step, to measure the amount of specimen in, compare it with the amount of specimen out, and determine whether there may have been any loss.

The scope of the invention is determined by the appended claims and is not intended to be limited by the specific embodiment shown and described.

I claim:

1. A dialyzer comprising a vertical central shaft, a lower clamp unit adjustably and selectively fixedly mounted to said shaft,
   an upper clamp unit adjustably and selectively fixedly mounted on said shaft,
   said lower clamp unit comprising a lower clamp block having sides, and a clamp bar attached to and opposed to each of said sides, each of said bars being selectively clampable against said side, and circulating pumping means in said lower clamp block comprising an opening through said lower clamp block, said opening being slanted, said upper clamp unit comprising an upper clamp block having sides, a bar opposed to each of said sides, a plurality of vertically aligned grooves in each of said bars and each of said sides, each of said grooves in a said bar being opposed to a said groove in said block side to form a vertical channel when said bar is clamped to said block.

2. A dialyzer as set forth in claim 1 wherein said lower clamp block has an upper face and a lower face, and said circulating pumping means comprises said opening extending from said upper face to said lower face, said opening lying substantially in a plane parallel to the plane of said central shaft.

3. A dialyzer as set forth in claim 2 wherein a pair of said openings is provided in said lower clamp block. The said slant of each of said openings being oppositely disposed from the vertical.

4. A dialyzer as set forth in claim 1 wherein each of said upper clamp bars and lower clamp bars is adjustably fixed to its upper clamp block or lower clamp block respectively by a clamp bolt, said clamp bolt passing through said bar and into a threaded socket in said block.

5. A dialyzer as set forth in claim 4 wherein a helical spring is provided around each said bolt, between said bar and said side of said block, and said bar is provided with a recess on the face thereof opposed to said block side, said recess accommodating and retaining said spring.

6. A dialyzer as set forth in claim 1 wherein said upper clamp central block is square in horizontal configuration, each side of said block being provided with three vertically aligned grooves, each said groove being substantially semicircular, each said side of said central block being provided with a said clamping bar permanently affixed thereto and selectively positionable into clamping or non-clamping mode, each said bar having an inner face, each said inner face being provided with three vertically aligned grooves, each of substantially semicircular shape, the said grooves on said bars and said block being positioned to oppose each other and together form a plurality of substantially circular vertically aligned channels.

7. A dialyzer as set forth in claim 6 wherein said lower central block is square in horizontal configuration and is provided with a circulating pump means therein, said pump means comprising at least one opening therethrough, said opening being in a plane parallel to a side of said square an oriented with the longitudinal axis thereof displaced from the vertical.

8. A dialyzer as set forth in claim 7 wherein the plurality of elongated open-ended dialysis bags are mounted on said dialyzer, each said bag being vertically oriented, clamped adjacent the bottom thereof between said lower clamp central block and a lower clamp bar, the upper end of said bag each passing through said channel formed between said upper clamp central block and said upper clamp bar.

9. A dialyzer as set forth in claim 8, wherein each said dialyzer bag is provided with a rigid filling tube inserted into the upper end of said bag, said filling tube extending above said bag and above said upper clamp, and extending through said channel.

10. A dialyzer as set forth in claim 9 wherein each edge of each central block and clamping bar which comes in contact with a dialyzer bag is provided with a chamfer, and in which said central shaft is stainless steel and said central blocks and bars are of methyl methacrylate.

11. A dialyzer system in which a dialyzer as set forth in claim 10 has a chuck at the upper end of said central shaft, a container for dialyzer bath, a motor provided above said container and above said chuck, means connecting said motor to said chuck to suspend said dialyzer in said container out of contact therewith, and to rotate said container.

12. A method of dialysis comprising providing a vertically aligned array of a plurality of dialysis bags around the complete periphery of a dialyzer mounting means, rotating said dialyzer mounting means and said array of bags in a dialyzer bath, said rotation of said monting means providing a circulating pumping action of liquid contained in said bath upwardly into that volume of said bath bounded on the sides by said array of dialyzer bags by causing an inclined opening in the bottom of said mounting means to circulate dialyzer bath liquid into the volume of bath liquid bounded by said array of dialyzer bags.

13. A dialysis method as set forth in claim 12 wherein each of said bags is clamped and sealed at the bottom thereof and clamped at the top thereof to said dialysis mounting means, and a rigid-walled opening is provided through the top of each of said bag, before said bag is filled with specimen to be dialyzed.

14. A method of dialysis as set forth in claim 13 wherein each of said dialyzer bags is filled with specimen to be dialyzed by insertion into said rigid walled tube of a syringe needle, said specimen being injected into said bags by depression of the plunger of said syringe.

15. A method of dialysis as set forth in claim 14 wherein each of said bags is inflated by forcing air through said rigid-walled opening at the top thereof before said bag is filled with specimen to be dialyzed.

16. A method of dialysis as set forth in claim 15 wherein, after said bags are attached to said dialyzer, and after said inflation, and after said filling, and after said rotation resulting in at least partial completion of said dialysis, said rotation is stopped, and at least part of said specimen from a bag is withdrawn while said bag remains clamped and sealed at the bottom thereof and clamped at the top thereof to said dialysis mounting means.

* * * * *